(12) United States Patent
Wiese et al.

(10) Patent No.: US 6,281,372 B1
(45) Date of Patent: Aug. 28, 2001

(54) PROCESS FOR SYNTHESIS OF VINYL ESTERS FROM BUTENE OLIGOMERS

(75) Inventors: Klaus-Diether Wiese; Paul Olbrich, both of Haltern; Juergen Gabriel, Dorsten, all of (DE)

(73) Assignee: OXENO Olefinchemie GmbH, Marl (DE)

( * ) Notice: Subject to any disclaimer, the term of this patent is extended or adjusted under 35 U.S.C. 154(b) by 0 days.

(21) Appl. No.: 09/514,355

(22) Filed: Feb. 28, 2000

(30) Foreign Application Priority Data

Feb. 26, 1999 (DE) .............................. 199 08 320

(51) Int. Cl.$^7$ .................................. C07C 51/00
(52) U.S. Cl. .................. 554/128; 554/131; 560/232; 585/329
(58) Field of Search .................. 554/128, 131; 560/232; 585/329

(56) References Cited

U.S. PATENT DOCUMENTS 5,998,685 * 12/1999 Nierlich et al. ...................... 585/329

FOREIGN PATENT DOCUMENTS

| 2339947 | 2/1974 | (DE) . |
| 92/13818 | 8/1992 | (WO) . |
| 93/22353 | 11/1993 | (WO) . |
| WO 93/22353 | * 11/1993 | (WO) . |

OTHER PUBLICATIONS

V. Hübner, "Vinylierung Höherer Carbonsäuren an Katalysatorschmelzen", *Fette–Seifen–Anstrichmittel*, 1966, vol. 68 Jahrgang, No. 4, pp. 290–292.

Y. Souma et al., "Carbonylation of Alcohols, Olefins, and Saturated Hydrocarbons by Co in the Ag(I)–H$_2$SO$_4$ System", *Bulletin of the Chemical Society of Japan*, Jul., 1974, vol. 47(7), pp. 1717–1719.

"Polyvinylverbindungen", *Ullmanns Encyklopadie de Techmisclem Chemie*, Band 19, p. 368.

H. Bahrmann, "Koch Reactions", *New Synthesis with Carbon Monoxide*, Springer Verlag, Berlin 1980, pp. 372–413.

R. H. Friedlander et al., "Make Plasticizer Olefins Via N–Butene Dimerization", Hydrocarbon Processing, Feb. 1986, pp. 31–33.

Y. Chauvin et al., "Dimerization and Codimerization", *2.3 Reactions of Unsaturated Compounds*, 1996, pp. 258–264.

H.P.H. Scholten et al., "Recent Developments in Latices Based on Vinyl Esters of Branched Monocarboxylic Acids–Paper 1", Papers presented at the International Conference on "Water–Borne Coatings", Oct. 26, 1987.

C.E.L. Reader, Veova Latices for Modern Emulsion Paints, The Shell Chemical Company (Philippines) Inc., Jul. 1985.

H. Rinno, Poly(Vinyl Esters), *Ullmann's Encyclopedia of Industrial Chemistry*, 1993, vol A22, pp. 2–6.

"Polymer Properties and Uses", Vinyl Ester Polymers, *Encyclopedia of Polymer Science and Engineering*, Band 17, pp. 439–445, 1985.

H. Bahrmann, "Koch Reactions", New Synthesis with Carbon Monoxide, Springer Verlag, Berlin 1980, pp 372–413.*

Polymer Properties and Uses, Vinyl Ester Polymers, Encyclopedia of Polymer Science and Engeering, Band 17, pp. 425–439 (1985).*

Dam et al., A New Process for Making Carboxylic Acids, Chim. Ind. (Paris) v90, N.5. 511–14 (Nov. 1963).*

* cited by examiner

*Primary Examiner*—Ralph Gitomer
*Assistant Examiner*—Devesh Khare
(74) *Attorney, Agent, or Firm*—Oblon, Spivak, McClelland, Maier & Neustadt, P.C.

(57) ABSTRACT

A process for the synthesis of vinyl esters from butene oligomers, wherein butenes are oligomerized, the butene oligomers are separated from the oligomerized mixture, the butene oligomers are converted to carboxylic acids which are longer by one carbon atom, and the resulting carboxylic acids are converted to the corresponding vinyl esters. The butene oligomers are in particular dibutene, tributene and tetrabutene. The invention also relates to the use of the vinyl esters as plasticizers or as comonomers in polymerization reactions.

11 Claims, No Drawings

PROCESS FOR SYNTHESIS OF VINYL ESTERS FROM BUTENE OLIGOMERS

BACKGROUND OF THE INVENTION

1. Field of the Invention

The present invention relates to a process for synthesis of vinyl esters from butene oligomers, especially from dibutene and tributene, as well as the use of these vinyl esters.

2. Background of the Invention

Vinyl esters of tertiary carboxylic acids have long had a firm place in technology as comonomers, especially as internal plasticizers for the synthesis of environmentally safe, water-dispersable lacquers and inks on the basis of vinyl acetate. In addition to the action as plasticizers, they endow the copolymers with further advantageous properties such as high stability toward saponification, making the copolymers suitable for use under harsh conditions. Examples of such applications are as outdoor paints and thermally insulating surfacings of buildings.

The plasticizing properties of the vinyl esters, especially of tertiary carboxylic acids, depend on their chain length and on the type and position of the branches. One measure for the internal plasticization of copolymers is the glass transition temperature of the corresponding homopolymer. A comparison of the plasticizing properties of vinyl esters of various chain lengths by means of the glass transition temperature $T_g$ of the respective homopolymer reveals how it depends on molecular weight and on the degree of branching:

| Chain length of the carboxylic acid | Straight-chain vinyl ester | Glass transition temperature [° C.] | Tertiary vinyl ester | Glass transition temperature [° C.] |
|---|---|---|---|---|
| $C_2$ vinyl ester | Vinyl acetate | +38 (33)* | | |
| $C_3$ vinyl ester | Vinyl propionate | −7 (−7)* | | |
| $C_4$ vinyl ester | Vinyl butyrate | −5 | | |
| $C_5$ vinyl ester | | −15*** | 2,2-Dimethyl-propanoic acid | 86 (70)* |
| $C_6$ vinyl ester | Vinyl hexanoate | −20 | 2,2-Dimethyl-butanoic acid | 41*** |
| $C_{10}$ vinyl ester | Vinyl decanoate | −60 | | |
| $C_{12}$ vinyl ester | Vinyl laurate | −75 (−53)* | | |

(Encyclopedia of Polymer Science and Engineering, Vol. 17, p. 439 (1989), J. Wiley & Sons, Inc.),
(*Ullman's Encyclopedia of Industrial Chemistry, Vol. A22, p. 2, 5th Ed. (1993), Verlag Chemie),
(**C. E. L. Feeder, Surface Coatings Austral. 228, 1985), 8, pp. 11–16,
(***measured by applicants).

These values are suitable only as data for comparison with one another, since they can vary with the method of synthesis of the test compound and with the test method. Nevertheless, it is evident that the plasticizing properties improve with increasing chain length of the vinyl ester (up to an alkyl group containing 12 carbon atoms in the case of straight chains). In particular, the vinyl esters of straight-chain carboxylic acids have very good plasticizing properties, but because they can be readily saponified they are not very suitable for many applications.

In contrast, the vinyl esters of tertiary carboxylic acids can be used for diverse purposes, since they are extremely stable to saponification, temperature and oxidation. On the other hand, the tertiary branch drastically reduces the plasticizing effect, and further branches in the chain lead to further deterioration, as the following examples of homopolymers of vinyl esters of tertiary $C_9$ carboxylic acids show:

| Tertiary $C_9$ carboxylic acids | Glass transition temperature (° C.) |
|---|---|
| 2,3-Dimethyl-2-isopropylbutanoic acid | 119 |
| 2-Ethyl-2,3,3-trimethylbutanoic acid | 115 |
| 2,2,3,3-Tetramethylpentanoic acid | 91 |
| (VeoVa ® 9, Shell) | 70 (60)* |
| 2,4,4-Tetramethylpentanoic acid | 55 |
| 2,2,4-Trimethylhexanoic acid | 10 |

(H. P. H. Scholten, J. Vermeulen, W. J. van Westrenen, Recent development in latices based on vinyl esters of branched monocarboxylic acids, 7th International Conference on "Water-Borne Coatings", 26–28 October 1998, Penta Hotel, London),
(*W. Lau, VeoVa ®, Vinyl Ester Monomer Polymers DotCom Magazine, Vol. 2, No. 2, Feb. 1996).

The compounds most commonly used in modern industry are vinyl esters synthesized from a mixture of tertiary $C_{10}$ carboxylic acid isomers, which form homopolymers having a glass transition temperature of −3° C. As an example, this mixture is highly suitable for use and is in great demand as an internal plasticizer for polyvinyl acetate, in which it simultaneously increases the stability toward saponification.

The $C_{10}$ carboxylic acid used for synthesis of the vinyl ester is in turn synthesized by addition of carbon monoxide and water to tripropene under pressure and catalysis with extremely acid catalysts (hydrocarboxylation, especially by the Koch reaction).

Tripropene, finally, a mixture of isomeric $C_9$ olefins, is obtained in a mixture with other olefin fractions ($C_6$, $C_{12}$ and $C_{15}$ olefins by acid-catalyzed oligomerization of propene). Examples of suitable catalysts for this purpose are acid zeolites or phosphoric acid on a solid support.

One disadvantage in the process for synthesis of vinyl esters of $C_{10}$ carboxylic acids is that propene represents a relatively expensive raw material. Furthermore, considerable losses of raw material can be expected as a result of byproduct formation in the acid-catalyzed oligomerization of propene. Finally, it must be pointed out that the number of isomers in the tripropene fraction of the oligomer is already so large that even analytical control is difficult. The conversion to carboxylic acids ultimately leads to such a large number of isomers that it is difficult to define the properties of the resulting product mixture.

Some vinyl esters of tertiary carboxylic acids with more than 10 C atoms have been studied (for example, WO 93/22353). Certainly they all have plasticizing ability, as can be expected from their relatively long carbon chain. On the one hand, however, the necessary raw materials are in many cases not available in sufficient quantities at a reasonable price and, on the other hand, incompatibility in the copolymer becomes progressively worse with increasing chain length.

Some vinyl esters of tertiary carboxylic acids with fewer than 10 C atoms are also known and have been studied with regard to their suitability as plasticizers. For example, the vinyl esters based on pivalic acid (a tertiary $C_5$ acid) and on tertiary $C_9$ acids (VeoVa® 9) have a certain industrial importance, but in both cases they represent comonomers having a hardening effect compared with vinyl acetate.

It would therefore be desirable to exploit raw material sources other than propene or its oligomers for the synthesis of vinyl esters which have plasticizing properties equal to or better than those of the vinyl esters of, for example, the $C_{10}$ carboxylic acids based on tripropene.

SUMMARY OF THE INVENTION

The present invention is based on the surprising discovery that tertiary carboxylic acids synthesized from butene oligomers are extremely suitable as plasticizers.

Thus, the present invention provides a process for synthesis of vinyl esters, comprising:

(a) oligomerizing butenes, (b) separating the butene oligomers from the oligomerized mixture from (a), (c) converting the separated butene oligomers to carboxylic acids which are longer by one carbon atom, and (d) converting the carboxylic acids to the corresponding vinyl esters.

The vinyl esters synthesized by the inventive process are extremely suitable as comonomers for the synthesis of internally plasticized polymers. Examples are the copolymerization of the $C_9$ carboxylic acid vinyl ester with vinyl chloride, or the copolymerization with vinyl acetate. Terpolymers containing acrylates are also a potential area of application. Under these conditions the proportion of vinyl esters synthesized according to the invention can be varied over wide limits, depending on the desired properties. They can also be used in the form of homopolymers if, for example, particularly compliant films are to be made.

A more complete appreciation of the invention and many of the attendant advantages thereof will be readily obtained as the same becomes better understood by reference to the following detailed description.

DETAILED DESCRIPTION OF THE INVENTION

The first step of the process according to the invention is oligomerization of butenes, producing mainly dibutene ($C_8$ olefin). Also formed are tributene ($C_{12}$ olefin) and tetrabutene ($C_{16}$ olefin) by trimerization and tetramerization respectively of butene. For this purpose there can be used as raw materials all industrial streams containing $C_4$ olefin, such as $C_4$ cracked gas, $C_4$ olefins from Fischer-Tropsch syntheses, and $C_4$ olefins from dehydrogenation of butane, or from other industrial processes.

Thus dibutene, tributene, tetrabutene or even higher oligomers can be used as butene oligomers in the process according to the invention. Separation of the butene oligomers from the oligomer mixture can be achieved by simple procedures and in high purity by distillation.

The process of the present invention can therefore be used both for synthesis of $C_9$ carboxylic acid vinyl esters from dibutene or from the corresponding $C_9$ carboxylic acids and for synthesis of $C_{13}$ carboxylic acid vinyl esters from tributene or from the corresponding $C_{13}$ carboxylic acids.

Obviously it is necessary to use for oligomerization largely straight-chain $C_4$ streams, or in other words containing a high proportion of n-butenes, in order to obtain vinyl esters with little branching.

In the standard procedure, butadiene is first removed from the raw $C_4$ cracked gas by extraction or is converted to straight-chain butenes by selective hydrogenation. In the present case, selective hydrogenation is not absolutely necessary, but is particularly favorable, since it considerably increases the proportion of n-butenes for oligomerization. In both cases there is obtained a butadiene-free $C_4$ cut, known as raffinate I. In the next step isobutene can be removed from the $C_4$ stream by, for example, synthesis of methyl tert-butyl ether (MTBE) by reaction with methanol. MTBE is in demand as a component of motor fuels. Other possibilities are reaction of the isobutene from raffinate I with water to obtain TBA (tert-butanol) or acid-catalyzed oligomerization of the isobutene to obtain diisobutene. The resulting $C_4$ cut, which is known as raffinate II and is now free of isobutene, now contains only 1-butene and 2-butene, as desired. Alternatively, 1-butene itself can be obtained by distillation, and the cut freed of 1-butene is then known as raffinate III.

Simple distillative separation of the isobutene from a $C_4$ cut, followed by further processing, is normally not possible, since 1-butene and isobutene have almost identical boiling points. On the other hand, distillative separation of 2-butene and isobutene is possible. Thus, the conversion of 1-butene by hydroisomerization into 2-butene means that the simple distillative separation of isobutene is a feasible approach to obtaining $C_4$ streams which now contain only straight-chain butenes.

Raffinate II or III is preferably used for oligomerization of butene to dibutene. Other industrial $C_4$ streams are also usable provided they do not contain other unsaturated compounds in addition to the straight-chain butenes. The especially preferred feedstock for butene oligomerization is n-butene, since the vinyl esters of tertiary carboxylic acids synthesized therefrom have better plasticizer properties, as proved by the examples.

On the other hand, if the plasticizing effect of the vinyl esters is a less important consideration, or if a hardening effect is actually desired, isobutene-containing $C_4$ streams can be used; a preferred feedstock is then raffinate I.

By virtue of the process according to the invention, it is possible to use economic raw materials for the synthesis of vinyl esters by means of industrially available $C_4$ streams which in many situations heretofore have had no utility whatsoever for chemical purposes.

The oligomerization of butene-containing $C_4$ streams to mixtures containing $C_8$, $C_{12}$ higher olefins is basically known. In principle there are three versions of the process.

Oligomerization on acid catalysts has long been known. Zeolites or phosphoric acid on supports are examples of catalysts used in industry. The products are mixtures of branched olefin isomers. Even under optimized conditions, dimethylhexenes are still the main product (WO 92/13818).

As shown in the Examples below, the $C_8$ olefins separated under these conditions can be processed to the corresponding tertiary carboxylic acids and their vinyl esters. Unfortunately, there are obtained only homopolymers with a high glass transition temperature, meaning that the comonomers have poor plasticizing ability or even have a hardening effect.

Another process practiced worldwide is oligomerization with soluble nickel complexes, known as the DIMERSOL process (see Yves Chauvin, Helene Olivier; in "Applied Homogeneous Catalysts with Organometallic Compounds"; edited by Boy Cornils, Wolfgang A. Herrmann; Verlag Chemie, 1996, 258–268, incorporated herein by reference). The vinyl esters of $C_9$ carboxylic acids synthesized from the $C_8$ fraction have a much better plasticizing effect than the vinyl esters produced by the cited process (see the Examples below).

Finally, oligomerization on fixed-bed nickel catalysts by the process of OXENO OLEFINCHEMIE GmbH is also important. The process has found its way into the literature as the OCTOL process (Hydrocarbon Process., Int. Ed. (1986) 65 (2, Sect. 1, 31–33, incorporated herein by reference). The tertiary carboxylic acids synthesized therefrom can be converted to vinyl esters, which bring about particularly good internal plasticization in copolymers.

The use of butene oligomers, especially dibutene and tributene, for synthesis of vinyl esters offers several noteworthy advantages.

Inexpensive industrial $C_4$ streams such as raffinate II, raffinate III or other raw materials containing $C_4$ olefins can be used as raw materials. The cuts such as raffinate II or III containing substantially only n-butenes as oligomerizable components are particularly suitable for synthesis of comonomers for internal plasticization. It was particularly surprising and unexpected that the vinyl esters synthesized according to the invention on the basis of tertiary $C_9$ carboxylic acids obtained from dibutene have excellent plasticizing effect for copolymerization with vinyl acetate or vinyl chloride, the result being at least equivalent to that of the standard product based on tripropene, And yet another improvement can be achieved with the correspondingly synthesized vinyl esters based on tributene.

In the process of the present invention, the butene oligomers are separated from the oligomerization product and converted respectively to the corresponding carboxylic acids which are longer by one carbon atom. This can be achieved by acid-catalyzed hydrocarboxylation (Koch reaction) or by hydroformylation and subsequent oxidation of the resulting oxo aldehydes. The Koch synthesis, as described in Falbe ("New Synthesis with Carbon Monoxide", Springer Verlag, Berlin, 1980, pp. 372 ff., incorporated herein by reference), will in practice be the preferred method. In this process, olefins are reacted with carbon monoxide in the presence of strong acids such as sulfuric acid or boron fluoride hydrates to obtain tertiary carboxylic acids. With $Cu^+$ as cocatalyst, the reaction even takes place under normal pressure and ambient temperature (Y. Souma, H. Sano; Bull. Chem. Soc. Jpn. 1974, 47, 1717, incorporated herein by reference).

Thereafter the carboxylic acids obtained in this way are converted to the corresponding vinyl esters. This can be achieved, for example, by reacting the carboxylic acids with acetylene at normal pressure and 200 to 250° C., preferably in the presence of the zinc salt of the acid to be vinylated (for example, according to Encyl. Polym. Sci. Eng. 17, pp. 426–434, incorporated herein by reference).

Alternatively, the vinyl esters can be obtained by transesterification of the carboxylic acids with further vinyl esters such as vinyl acetate or vinyl propionate (as described, for example, in: Ullman, 4th Edition, Volume 19, pp. 368 ff., incorporated herein by reference).

As discussed above, the plasticizing properties of the vinyl esters are influenced by their degree of branching. In turn, the degree of branching of the vinyl esters can be influenced by the degree of branching of the feed olefins. In special embodiments of the present invention, therefore, there can be used dibutenes with a proportion of multiply branched olefins such as dimethylhexene not exceeding 35 wt %, preferably 25 wt %.

The vinyl esters synthesized by the process according to the invention can be used as comonomers in polymerization reactions, such as the synthesis of polyvinyl acetate, where they bring about internal plasticization with simultaneous increase in stability toward hydrolysis. Copolymerization with ethylene, or synthesis of terpolymers containing acrylates, are further practical examples of the use of the vinyl esters synthesized according to the invention as comonomers for internal plasticization.

EXAMPLES

Having generally described this invention, a further understanding can be obtained by reference to certain specific examples which are provided herein for purposes of illustration only and are not intended to be limiting unless otherwise specified.

Examples 1 to 3

Hereinafter there is indicated the typical composition of dibutenes formed from n-butenes by the three different oligomerization processes. In this connection the product composition depends substantially only on the oligomerization process. It is possible to use, for example, raffinate II or raffinate III or other streams which contain n-butenes, provided they do not contain substantial quantities of branched butenes. Raffinate III was used as raw material in the following examples.

| Olefin A | Dibutene, obtained by oligomerization of raffinate III on montmorillonite (acid catalysis) |
| Olefin B | Dibutene, obtained by oligomerization of raffinate III by the DIMERSOL process |
| Olefin C | Dibutene, obtained by oligomerization of raffinate III by the OCTOL process |

|  | Example 1 Olefin A | Example 2 Olefin B | Example 3 Olefin C |
| --- | --- | --- | --- |
| n-Octene | ~0% | ~6% | ~13% |
| 3-Methylheptene | ~5% | ~59% | ~62% |
| 3,4-Dimethylhexene | ~70% | ~34% | ~24% |
| Other $C_8$ olefins | ~25% | ~1% | ~1% |

The proportion of straight-chain olefins and olefins with at most one branching point is therefore about 5% for olefin A, 65% for olefin B and about 75% for olefin C. All values are in wt %.

Examples 4 to 6

Using the procedure of German Patent DE 2339947, incorporated herein by reference, tertiary carboxylic acids were synthesized from olefins A, B and C. A complex of boron fluoride and water was used as catalyst and $Cu^+$ as cocatalyst. The reactions were performed in a stirred autoclave in a temperature range of 20 to 35° C. and a CO pressure of 30 bar. In the process, the olefin was introduced at constant rate for a period of 6 hours. The pressure was maintained constant by a make-up supply of CO. The reaction was ended as soon as further CO uptake was no longer observed.

After separation from the catalyst phase, washing with water and distillative processing of the raw carboxylic acids, there were obtained products of the following composition, in each case over several batches (values in wt %).

| C₉ carboxylic acid isomers | Example 4 Acid A | Example 5 Acid B | Example 6 Acid C |
|---|---|---|---|
| 2,2-Dimethylheptanoic acid | 0.5% | 6.5% | 7.4% |
| 2-Methyl-2-ethylhexanoic acid | 3.7% | 48.1% | 55.2% |
| 2-Methyl-2-propylpentanoic acid | 0.5% | 6.3% | 7.2% |
| 2,2-Diethylpentanoic acid | 0.2% | 3.0% | 3.5% |
| 2,2,5-Trimethylhexanoic acid | 2.1% | 1.1% | 0.8% |
| 2,2,4-Trimethylhexanoic acid | 2.0% | 1.0% | 0.8% |
| 2,4-Dimethyl-2-ethylpentanoic acid | 4.4% | 2.2% | 1.6% |
| 2,2,3-Trimethylhexanoic acid | 6.4% | 3.2% | 2.4% |
| 2-Methyl-2-isopropylpentanoic acid | 13.7% | 6.9% | 5.1% |
| 2,3-Dimethyl-2-ethylpentanoic acid | 37.5% | 19.0% | 13.8% |
| 2-Ethyl-2-isopropylbutanoic acid | 3.0% | 1.5% | 1.1% |
| Unknown other acids | 25.8% | 1.2% | 1.3% |

The mixtures of tertiary carboxylic acids obtained in Examples 4 to 6 were reacted with acetylene at normal pressure and a temperature of 190 to 220° C. in the presence of the zinc salt of the respective acid to be converted according to the following equation:

$$R\text{—}COOH + HC\equiv CH \rightarrow R\text{—}COO\text{—}CH=CH_2$$

The reaction was carried out by the method of G. Huebner, Fette, Seifen, Anstrichmittel, 68 (4), pp. 290–292 (1966), incorporated herein by reference.

After distillation of the raw product, vinyl esters with a purity of ≧99.8% were obtained. According to gas chromatography, these have a degree of branching substantially comparable or even identical to that of the carboxylic acids. The vinyl esters obtained in this way are referred to hereinafter as vinyl ester A (based on acid A, Example 7), vinyl ester B (based on acid B, Example 8), and vinyl ester C (based on acid C, Example 9).

Examples 10 to 14

From the vinyl esters according to Examples 7 to 9 there were synthesized homopolymers by standard procedure (Examples 12 to 14) and their glass transition point was determined as a measure of their suitability as copolymers for internal plasticization.

| Feedstocks | |
|---|---|
| Monomer | Parts by weight |
| Vinyl esters of C₉ carboxylic acids | 100.00 |
| Aqueous phase | |
| Demineralized water | 70.00 |
| Anionic surfactant, such as Marlon ® A 390 (85% active substance) | 0.03 |
| Nonionic surfactant, such as Marlophen ® 820 (25% solution) | 8.00 |

| Feedstocks | |
|---|---|
| Monomer | Parts by weight |
| Potassium peroxydisulfate (K₂S₂O₈) | 0.10 |
| Potassium carbonate | 0.25 |
| Hydroxyethylcellulose, such as Natrosol 250 L (or LR) | 2.00 |
| Acetic acid (100%) | 0.20 |
| Initiator solution | |
| Potassium peroxydisulfate | 0.23 |
| Demineralized water | 12.00 |

Procedure

The aqueous phase and about 10% of the monomers were heated with stirring to 75° C. After 15 minutes at this temperature, the remaining monomers and the initiator solution were introduced in separate streams. The monomers were introduced at constant rate within 120 minutes and the initiator solution within 135 minutes. During the addition process, the temperature was maintained between 75 and 80° C. After a further 120 minutes of stirring at the same temperature, the mixture was cooled to room temperature. From the resulting emulsion there were made, if necessary after filtration, molded articles, the glass transition temperatures of which were determined by torsional vibration analysis (by the method of DIN 53445, incorporated herein by reference).

In addition, two commercial vinyl esters having known glass transition temperatures were subjected to the same procedure, in order to ensure comparability of the test method. The first of these was a vinyl ester from tertiary C₁₀ acids (VeoVa®10, based on tripropene, Comparison Example 10), which is widely used as an internal plasticizer for vinyl acetate, for example. The other was a commercial vinyl ester from tertiary C₉ acids (VeoVa®9, Comparison Example 11), or in other words a vinyl ester with the same empirical formula as the vinyl esters synthesized in the foregoing examples, but with a different degree of branching.

The following data were measured:

| Feed | Example 10 (comparison) | Example 11 (comparison) | Example 12 From acid A | Example 13 From acid B | Example 14 From acid C |
|---|---|---|---|---|---|
| Glass transition temperature | −3° C. | ~+60° C. | ~+38° C. | +1° C. | −3° C. |

Vinyl ester A based on acid-catalyzed oligomerized butene is therefore a comonomer with hardening effect. Vinyl ester B from butene oligomerized by the DIMERSOL process is already a plasticizing comonomer. With vinyl ester C, synthesized from dibutene by the OCTOL process, there is achieved an excellent plasticizing effect, equivalent to that of the comparison product based on tripropene (Comparison Example 10). It is interesting to compare Example 11 with Example 14. In both cases there were used vinyl esters of tertiary carboxylic acids with 9 C atoms, or in other words with the same empirical formula. An excellent plasticizing effect is achieved with the vinyl ester of Example 14 synthesized according to the invention, whereas Comparison Example 11 results in a comonomer with pronounced hardening effect.

Example 15

Raffinate III was oligomerized by the OCTOL process (see Example 3). The tributene was separated from the oligomer mixture and a $C_{13}$ carboxylic acid mixture was synthesized by the KOCH synthesis (by analogy with Examples 4 to 6). This mixture was reacted with acetylene to obtain the corresponding vinyl esters, as described in Examples 7 to 9. From the resulting vinyl ester mixture there was synthesized a homopolymer by analogy with the procedure of Examples 10 to 14; this had a glass transition temperature of −13° C. The vinyl ester of the $C_{13}$ carboxylic acid based on tributene therefore has an extremely good plasticizing effect despite the high degree of branching.

Obviously, numerous modifications and variations of the present invention are possible in light of the above teachings. It is therefore to be understood that within the scope of the appended claims, the invention may be practiced otherwise than as specifically described herein.

This application is based on German Patent Application Serial No. 19908320.7, filed on Feb. 26, 1999, and incorporated herein by reference in its entirety.

What is claimed is:

1. A process for synthesis of vinyl esters from butene oligomers, comprising:
   (a) oligomerizing butenes on a fixed bed nickel catalyst,
   (b) separating the butene oligomers from the oligomerized mixture from (a),
   (c) converting the separated butene oligomers to carboxylic acids which are longer by one carbon atom, and
   (d) converting the carboxylic acids to the corresponding vinyl esters.

2. A process according to claim 1, wherein the butene oligomers are converted by acid-catalyzed hydrocarboxylation to carboxylic acids which are longer by one carbon atom.

3. A process according to claim 1, wherein the conversion of the butene oligomers to carboxylic acids which are longer by one carbon atom is accomplished by hydroformylation and subsequent oxidation of the resulting aldehydes.

4. A process according to claim 1, wherein the carboxylic acids are reacted with acetylene in (d).

5. A process according to claim 4, wherein the carboxylic acids are reacted with acetylene in the presence of a zinc salt of the carboxylic acid in (d).

6. A process according to claim 1, wherein the vinyl esters are obtained by transesterification of other vinyl esters with the carboxylic acids.

7. A process according to claim 6, wherein the other vinyl esters are vinyl acetate or vinyl propionate.

8. A process according to claim 1, wherein the butene oligomers are dibutenes, which are converted to $C_9$ carboxylic acids, and then to the corresponding vinyl esters.

9. A process according to claim 1, wherein the butene oligomers are tributenes, which are converted to $C_{13}$ carboxylic acids, and then to the corresponding vinyl esters.

10. A process according to claim 1, wherein the dibutenes do not contain more than 35 wt % of multiply branched olefins.

11. A process according to claim 10, wherein the dibutenes do not contain more than 25 wt % of multiply branched olefins.

* * * * *